United States Patent [19]

Brima et al.

[11] Patent Number: 4,980,513
[45] Date of Patent: Dec. 25, 1990

[54] PROCESS FOR MAKING A HYDROCARBYL VINYL KETONE

[75] Inventors: Thomas S. Brima, Cincinnati; Ronnie M. Hanes, Loveland, both of Ohio

[73] Assignee: Quantum Chemical Corporation, New York, N.Y.

[21] Appl. No.: 460,778

[22] Filed: Jan. 4, 1990

[51] Int. Cl.$^5$ .............................................. C07C 45/70
[52] U.S. Cl. .................................... 568/391; 568/315; 568/389
[58] Field of Search ................ 568/389, 391, 347, 315

[56] References Cited

U.S. PATENT DOCUMENTS

| | | | |
|---|---|---|---|
| 3,361,828 | 1/1968 | Robbins et al. | 568/391 |
| 4,562,296 | 12/1985 | Hargis | 568/391 |
| 4,618,725 | 10/1986 | Lenz | 568/391 |

FOREIGN PATENT DOCUMENTS

| | | | |
|---|---|---|---|
| 60-100534 | 6/1985 | Japan | 568/391 |
| 62-187422 | 8/1987 | Japan | 568/391 |

OTHER PUBLICATIONS

CA Selects: Catalysis (Organic Reactions) Issue 10, 1988, Abstract 108:166978y of Japanese Patent Publication 62-273,933.
Ueda et al., *J. Chem. Soc., Chem. Commun.*, 39-40 (1984).
Hassouni et al., *Stud. Surf. Sci. Catal.*, 41, 307-315 (1988).
Okada et al., Chemistry Letters, 333-334 (1973).
Wang et al, Chem. Abst., vol. 110, #156445z (1989).
Kurokawa et al, Chem. Abst., vol. #233,139m (1988).
Ueda et al, Chem. Abst., vol. 104, #110219b (1986).

*Primary Examiner*—James H. Reamer
*Attorney, Agent, or Firm*—Kenneth D. Tremain; Gerald A. Baracka

[57] ABSTRACT

A process for making a hydrocarbyl vinyl ketone is disclosed. In this process a ketone having the structural formula $CH_3COR$, where R is lower alkyl, phenyl or $C_7$-$C_8$ aralkyl, is reacted with methanol in an oxygen-containing atmosphere in the presence of a catalyst system comprising a catalytically effective amount of iron on an inert support. In another preferred embodiment, the catalyst system comprises a catalytically effective amount of a precious metal selected from the group consisting of silver and gold, in addition to iron, supported on an inert material.

27 Claims, No Drawings

PROCESS FOR MAKING A HYDROCARBYL VINYL KETONE

BACKGROUND OF THE INVENTION

1. Field of the Invention

The present invention is directed to a new process for making a hydrocarbyl vinyl ketone. Hydrocarbyl vinyl ketones, especially the most commercially significant of this class of compounds, methyl vinyl ketone, have commercially significant applications. Among these applications are their use as monomers in the copolymerization of photodegradable plastics. That is, when monomers used in the formation of polyethylene-type plastics are copolymerized with a hydrocarbyl vinyl ketone, i.e., methyl vinyl ketone, the copolymer product, a polyethylene-type plastic, not only possesses the same useful properties as the polyethylene plastic but, in addition, the otherwise non-degradable polyethylene plastic becomes photodegradable. Indeed, the rate of degradation of a copolymer of ethylene and methyl vinyl ketone is six times that of a typical ethylene-carbon monoxide copolymer, the class of ethylenic copolymers recognized as having the highest rate of photodegradability of commercially available ethylene copolymer plastics.

A major inhibiting factor in the commercialization of hydrocarbyl vinyl ketone-containing photodegradable copolymers is the high cost of these ketones. The most commercially important of these ketones, methyl vinyl ketone, is produced commercially by dimerization of acetylene to form vinyl acetylene. Hydration of vinyl acetylene produces methyl vinyl ketone.

In view of the high cost of this process attempts have been made to provide a catalytically induced single step process to reduce the cost of manufacturing this compound. However, these prior art processes have utilized catalysts in which the degrees of conversion and selectivity have not reached the level required for commercial exploitation. Therefore, there is a continuing need in the art to develop a commercially viable process which results in the formation of hydrocarbyl vinyl ketones.

2 Background of the Prior Art

Processes have been developed for the catalytic conversion of hydrocarbyl vinyl ketones. Of these prior art processes those most relevant to the present invention involve the catalytic condensation of a ketone with methanol to produce a hydrocarbyl vinyl ketone. This is a desirable process in that it involves a single step reaction to produce the desirable end product.

Such a process is taught in *C.A. Selects, Catalysis*, 108 (10), 166978y. This abstract of Japanese Patent Publication 62-273,933 to Mitsubishi Chemical Industries Inc. involves the dehydration-condensation of a ketone having the structural formula $RCH_2COR'$, where R is hydrogen or alkyl; and R' is alkyl, in the presence of niobium oxide. Specifically, acetone is treated with $Nb_2O_5 \cdot 2.44\ H_2O$ at 150° C. for one hour to yield a 14.4% conversion at 91.5% selectivity to methyl vinyl ketone.

Another reference relevant to the present invention is the disclosure of Ueda et al., *J. Chem. Soc., Chem. Commun.*, 39–40 (1984). This paper describes the preparation of methyl vinyl ketone by the catalytic reaction of a mixture of acetone and methanol at atmospheric pressure and elevated temperature in the presence of an iron-magnesia catalyst. The best result of the runs reported in this paper is a 12.1% conversion of acetone to produce methyl vinyl ketone at a selectivity of 54.5%. This reaction is conducted at a temperature of 350° C. and at atmospheric pressure.

Hassouni et al., *Stud. Surf. Sci. Catal.*, 41, 307–315 (1988) sets forth a process for synthesizing methyl vinyl ketone from methanol utilizing a copper, silver or zinc catalyst. In a preferred embodiment this reference discloses the formation of methyl vinyl ketone utilizing a silver on silica catalyst activated with an equimolar amount of potassium carbonate.

Whereas all of the above discussed references employ an oxygen-free atmosphere, Okada et al., *Chem. Letters*, 333–334 (1973) teaches the formation of methyl vinyl ketone by co-feeding acetone, methanol, oxygen and nitrogen gases in a molar ratio of 1:2.1:2.3:8.86, respectively, in the presence of a catalyst of silver on a silica-magnesia support. The requirement of employing a precious metal catalyst, rather than much cheaper iron, limits the attractiveness of the process of this disclosure.

BRIEF SUMMARY OF THE INVENTION

A new process has now been developed which results in the catalytic formation of a hydrocarbyl vinyl ketone. This process is characterized by relatively high conversion of the ketone reactant at very high selectivity to produce the desired ketone product. This desirable result is obtained by the utilization of a unique catalytic oxidation-condensation reaction distinguished from the catalytic processes advanced in the prior art.

In accordance with the present invention a process for making a hydrocarbyl vinyl ketone is disclosed. In this process a ketone having the structural formula $CH_3COR$, where R is a hydrocarbyl group, is reacted with methanol in an oxygen-containing environment and in the presence of a supported iron catalyst.

DETAILED DESCRIPTION

The process of the present invention, the formation of a hydrocarbyl vinyl ketone, involves the reaction of a ketone having the structural formula:

$$CH_3COR \qquad \qquad (I)$$

where R is a hydrocarbyl group. Preferably, the ketone compound having the structural formula I is characterized by R being lower alkyl, phenyl or $C_7$–$C_9$ aralkyl. More preferably, R, in structural formula I, has the meanings $C_1$–$C_4$ alkyl, phenyl or benzyl. Still more preferably, R is methyl or phenyl. Most preferably, R is methyl.

In addition to the ketone reactant having the structural formula I, the process involves reaction of a second reactant, methanol. These two reactants are combined in a catalytic reaction obviously involving the presence of a catalyst system. The catalytic system, provided in a catalytically effective amount, comprises iron on an inert metal oxide support in the presence of oxygen or an oxygen-containing gas. The iron, supported on an inert material, may be provided in the form of the elemental iron, an iron oxide, an iron salt or an organoiron compound. Of these forms, the oxide is preferred.

To provide the requisite presence of oxygen, the reaction, to form a hydrocarbyl vinyl ketone, is conducted in the presence of oxygen gas or an oxygen-containing gas, usually, air. In the event that oxygen gas is utilized, it is preferred to also use a diluent inert gas, such as argon or nitrogen.

In a preferred embodiment of the present invention, the catalyst system comprises, in addition to iron, a second catalytic species, also disposed on the inert metal oxide support. The second catalytic species is a precious metal selected from the group consisting of silver and gold. Of these two precious metals silver is preferred.

In the preferred embodiment wherein the catalyst system includes a precious metal species, independent of whether gold or silver is utilized, the metal may be present in elemental form, as a salt or as an oxide. Of these, the metal in elemental form or as an oxide is preferred.

It is emphasized that although both iron and, optionally, silver or gold is ultimately preferably present as an oxide or in elemental form, these metals are originally applied on the support as a salt. In the case of iron, the iron salt applied onto the support is water soluble. Of the water soluble iron salts, sulfate, nitrate and halide salts are preferred. Of these, iron chloride is particularly preferred.

In the preferred embodiment where a precious metal is employed, the preferred gold or silver salt is again water soluble. In the case of silver water soluble nitrate or sulfate salts are preferred. In the case of gold the chloride salt is most desirable. In each case the salt is converted to the oxide or the elemental form in an oxidation reaction. Usually, this oxidation reaction involves elevated heating of the metal salt, disposed on the support, in an oxygen-containing, i.e. air, atmosphere.

The catalyst system, as stated above, is preferably provided on a support. The support, upon which the iron and, optionally, the silver or gold is disposed, is an inert material. The inert material may be synthesized or may occur naturally. Whether manufactured or obtained from naturally occurring materials, a preferred class of inert materials useful in this application are the inert metal oxides. Such oxides as silica, alumina, zirconia, magnesia, beryllia and mixtures thereof are thus preferred. Natural ores, which include one or more of these oxides, with or without other materials, such as pumice and the like, are also within the scope of the inert materials within the contemplation of the catalyst system of the present invention. Of these inert metal oxides, alumina is particularly preferred for use as the catalyst support.

In the preferred embodiment wherein a supported catalyst is utilized, the iron concentration, based on the total weight of the supported catalyst, is usually in the range of between about 0.1 weight percent and about 15 weight percent. More preferably, the active constituent iron is present in a concentration in the range of between about 0.3 weight percent and about 10 weight percent. Still more preferably, the iron concentration of the supported catalyst is in the range of between about 0.75 weight percent and about 5 weight percent.

In the embodiment wherein the active components of the catalyst are iron and a precious metal selected from the group consisting of silver and gold disposed on an inert support, the catalyst system includes iron in the concentration ranges recited for the embodiment wherein iron is the sole catalytic agent. The silver or gold component, preferably the silver component, is present in a concentration in the range of between about 0.1 weight percent and about 3 weight percent, based on total weight of the supported iron and silver or gold catalyst. More preferably, the concentration of the precious metal, preferably silver, is in the range of between about 0.2 weight percent and about 2 weight percent, based on the combined total weight of the iron, the precious metal and the support.

The thermodynamic conditions under which this reaction occurs include a reaction temperature in the range of between about 250° C. and about 425° C. Preferably, the temperature of reaction is in the range of between about 300° C. and 375° C. The reaction occurs at a pressure in the range of between atmospheric and 50 psig. More preferably, the pressure of the reaction is in the range of between atmospheric and 25 psig. Still more preferably, the pressure of the hydrocarbyl vinyl ketone-forming reaction is atmospheric.

The process of the present invention preferably occurs by reacting 1 mole of a ketone having the structural formula I with between about 0.5 mole and 2.5 moles of oxygen. Similarly between about 4 moles and about 24 moles of methanol are present in the reaction per mole of ketone. More preferably, there are between about 1.75 moles and about 2.25 moles of oxygen present in the reaction per mole of ketone. In this more preferred embodiment between about 12 moles and about 20 moles of methanol are present in the reaction per mole of ketone having the structural formula I.

The following examples are provided to illustrate the scope of the present invention. Because these examples are given for illustrative purposes only, the invention should not be limited thereto.

EXAMPLE 1

Synthesis of Methyl Vinyl Ketone Using an Iron and Silver on Alumina Catalyst

A reactor for the synthesis of methyl vinyl ketone was prepared from a hollow glass tube (45 cm×2 cm i.d.) packed vertically with 20 cc. of 2 mm. glass beads supported on a glass wool plug. The plug served as a separator to separate the beads from a catalyst, whose composition is discussed below.

A glass thermowell was disposed down the middle of the reactor to the top of the glass bead portion. The reaction temperature was controlled by a temperature controller equipped with a control thermocouple taped onto the skin of the reactor at about the same vertical location as the inner thermocouple. The reactor was heated by a vertically mounted 33 cm. long tube furnace. The glass bead portion of the reactor was in the heating zone of the furnace.

The catalyst, disposed in the reactor, was iron-silver on alumina It was prepared by immersing the alumina in an aqueous solution of ferric chloride hydrate. That is, 35 g. of catalyst grade alumina pellets (⅛ in.×⅛ in.) were immersed in a solution formed by dissolving 2.0 g. $FeCl_3.6H_2O$ (7.3 mmoles) in 11 ml. of $H_2O$. The pellets turned yellow in the ferric chloride solution. The yellow pellets were dried under an air gun in a rotary dryer. When most of the water was evaporated the pellets gradually turned tan in color with the evolution of hydrogen chloride gas. After drying was complete the pellets were allowed to cool and then were submerged in a concentrated ammonium hydroxide solution for 45 minutes. The hydroxide solution was decanted and the pellets washed in running cold water for 30 to 45 minutes. The pellets were dried at room temperature followed by drying at 110° C.

The dried ferric chloride-containing alumina pellets were then disposed in a solution of silver sulfate in concentrated ammonium hydroxide (1.0 g. silver sulfate in 3 g. of concentrated ammonium hydroxide). The silver sulfate-treated pellets were dried in a rotary dryer under an air gun. The pellets were next calcined in an air circulating oven at 400° C. for four hours. The resultant catalyst was analyzed by atomic absorption and was found to comprise 1.1 weight percent iron and 0.9 weight percent silver, based on the total weight of the supported catalyst A volume of 30 ml. of the calcined pellets were charged into the reactor.

Initially, nitrogen and oxygen gases were mixed and fed into the top of the reactor. When the reactor temperature reached 20° C. below the desired reaction temperature, a solution of 8 g. acetone in 70.9 g. methanol was fed therein as a gaseous mixture. This reactant solution was introduced into the reactor by means of a syringe pump connected to the reactor through a rubber septum by means of a plastic tube. The gaseous reactant solution was fed into the reactor for between 10 and 20 minutes until the desired reaction temperature was reached. At this point the condensed liquid at the outlet, at the bottom of the reactor, was wiped and a product trap attached. The product trap comprised a U-tube (17.5 cm.×2 cm. i.d.) bathed in a dry ice-isopropyl alcohol slurry. The outlet of the trap was attached, by rubber tubing, to a smog bubbler which contained 10 ml. to 12 ml. diethyl ether. The bubbler was also bathed in a dry ice-isopropyl alcohol slurry. The volume of solution in the syringe pump was recorded and the reaction was officially begun.

The reaction was run for approximately 90 minutes. In the reaction, the reactant solution was fed into the reactor at a rate of 9.7 ml./hr. At the same time, nitrogen and oxygen gases were fed into the reactor at the respective rates of 100 cc/min and 10 cc/min, measured at standard conditions. The reactor, at the point when the reaction began, was maintained at 350° C., at which temperature the entire reaction was run. Thus, based on this elevated temperature, 11.4 cc./min., 183 cc./min., 228 cc./min. and 22.8 cc./min. of gaseous acetone, methanol, nitrogen and oxygen, respectively were introduced into the reactor. It is emphasized that the reactor was maintained at or about atmospheric pressure throughout the run. Based on calculations, known to those skilled in the art, the residence time for reaction of this gaseous stream was 4.04 seconds.

At the conclusion of 90 minutes, the reaction was concluded. At this time the trap was disconnected from the reactor, stoppered and the volume in the feeding syringe recorded. The disconnected product traps, which were removed from the slurry, were allowed to warm to room temperature with the primary trap still connected to the bubbler. The contents of the trap and the bubbler were then quantitatively transferred to a 25 ml. volumetric flask. The volume necessary to fill the 25 ml. flask was provided by ether washings.

This solution was analyzed on a Varian [trademark] 3700 gas chromatograph on Carbowax 20 M [trademark] 1400 column (10 in.×⅛ in.) at an oven temperature of 75° C. (9 min.) which was raised at increments of 5° C/min. to a final temperature of 140° C. Acetonitrile was used as the internal standard.

The above analysis provided the results summarized in the Table.

EXAMPLES 2 AND 3

Synthesis of Methyl Vinyl Ketone Using an Iron and Silver on Alumina Catalyst

Two additional examples were run in accordance with the procedure of Example 1. The results of these runs are summarized in the Table.

EXAMPLES 4 TO 7

Synthesis of the Methyl Vinyl Ketone Using an Iron on Alumina Catalyst

Example 1 was repeated but for the identity of the catalyst. In Examples 4 to 7 an iron on alumina catalyst was employed. The catalyst in each of Examples 4 to 6 was prepared by immersing alumina pellets (35 g.) of the type used in Example 1 in an aqueous ferric chloride solution (2.0 g. of $FeCl_3.6H_2O$ in 11 ml. $H_2O$). After drying in air, the iron on alumina pellets were submerged in a concentrated ammonium hydroxide solution for 45 minutes. The ammonium hydroxide solution was then decanted and the pellets washed in water for 30 to 45 minutes. An atomic absorption analysis of the iron on alumina catalyst established that the iron represented 0.51 percent by weight, based on the total weight of the supported catalyst. A charge of 30 ml. of these dried pellets were used as the catalyst in each of these examples.

The results of these runs are tabulated in the Table.

TABLE

| Exam No. | Catalyst | Acetone Chgd., mmoles | Acetone Rtd, mmoles | % Conv. | MVK Formed, mmoles | Select., % |
| --- | --- | --- | --- | --- | --- | --- |
| 1 | Fe—Ag on $Al_2O_3$ | 53.8 | 8.7 | 16.2 | 8.2 | 96.6 |
| 2 | Fe—Ag on $Al_2O_3$ | 57.9 | 9.0 | 15.5 | 8.4 | 95.6 |
| 3 | Fe—Ag on $Al_2O_3$ | 53.6 | 8.4 | 16.0 | 8.3 | 98.8 |
| 4 | Fe on $Al_2O_3$ | 38.1 | 6.9 | 18.1 | 5.7 | 82.6 |
| 5 | Fe on $Al_2O_3$ | 38.7 | 5.7 | 14.7 | 5.3 | 93.0 |
| 6 | Fe on $Al_2O_3$ | 41.0 | 7.1 | 17.3 | 6.9 | 97.2 |
| 7 | Fe on $Al_2O_3$ | 41.0 | 7.7 | 18.8 | 6.4 | 83.1 |

Notes
1. All runs conducted at atmospheric pressure and 350° C.
2. $O_2$ and $N_2$ fed at 10 cc/min and 100 cc/min, respectively, under standard conditions.
3. Each catalyst charge was 35 g.

The above embodiments and examples are given to illustrate the scope and spirit of the present invention. These embodiments and examples will make apparent, to those skilled in the art, other embodiments and examples. These other embodiments and examples are within the contemplation of the present invention. Therefore, the present invention should be limited only by the appended claims.

What is claimed is:

1. A process for making a hydrocarbyl vinyl ketone comprising reacting a ketone having the structural formula $CH_3COR$, where R is lower alkyl, phenyl or $C_7$-$C_8$ aralkyl, and methanol in an oxygen-containing atmosphere in the presence of a catalyst system which comprises a catalytically effective amount of iron on an inert support.

2. A process in accordance with claim 1 wherein said catalyst system includes a catalytically effective amount of a precious metal selected from the group consisting of silver and gold disposed on said inert support.

3. A process in accordance with claim 2 wherein said precious metal is silver.

4. A process in accordance with claim 1 where R is methyl or phenyl.

5. A process in accordance with claim 3 where R is methyl or phenyl.

6. A process in accordance with claim 1 where said inert support is an inert metal oxide.

7. A process in accordance with claim 2 where said inert support is an inert metal oxide.

8. A process in accordance with claim 2 wherein said inert support is alumina.

9. A process in accordance with claim 3 wherein said inert support is alumina.

10. A process in accordance with claim 1 wherein between about 0.5 mole and about 2.5 moles of oxygen and between about 4 moles and about 24 moles of methanol per mole of ketone are present in said reaction.

11. A process in accordance with claim 10 wherein between about 1.75 moles and about 2.25 moles of oxygen and between about 12 moles and about 20 moles of methanol are present per mole of ketone.

12. A process in accordance with claim 1 wherein said iron is present in a concentration in the range of between about 0.1 weight percent and about 15 weight percent, based on the total weight of said supported catalyst.

13. A process in accordance with claim 2 wherein said iron is present in a concentration in the range of between about 0.1 weight percent and about 15 weight percent and said precious metal is present in a concentration of between about 0.1 weight percent and about 3 weight percent, said percentages based on the total weight of said supported catalyst.

14. A process in accordance with claim 12 wherein said iron is present in a concentration in the range of between about 0.3 weight percent and about 10 weight percent.

15. A process in accordance with claim 13 wherein said iron is present in a concentration in the range of between about 0.3 weight percent and about 10 weight percent and said precious metal is present in a concentration in the range of between about 0.2 weight percent and about 2 weight percent.

16. A process for making a methyl vinyl ketone comprising reacting acetone and methanol in an oxygen-containing atmosphere in the presence of a catalyst system which comprises a catalytically effective amount of iron on an inert support.

17. A process in accordance with claim 16 where said reaction occurs at a temperature in the range of between about 250° C. and about 425° C. and at a pressure in the range of between atmospheric and about 50 psig.

18. A process in accordance with claim 17 wherein said reaction occurs at a temperature in the range of between about 300° c. and about 375° C. at a pressure of between atmospheric and about 25 psig.

19. A process in accordance with claim 18 wherein said iron is present as iron oxide.

20. A process in accordance with claim 18 wherein said inert support is alumina.

21. A process in accordance with claim 16 wherein said catalyst system includes a catalytically effective amount of a precious metal selected from the group consisting of silver and gold disposed on said inert support.

22. A process in accordance with claim 21 where said precious metal is silver.

23. A process in accordance with claim 22 wherein said silver is present as elemental silver or silver oxide.

24. A process in accordance with claim 23 wherein said inert support is alumina.

25. A process in accordance with claim 24 wherein said iron comprises about 1.1 weight percent and said silver comprises about 0.9 weight percent, based on the total weight of said supported catalyst.

26. A process for making methyl vinyl ketone comprising reacting acetone and methanol in an oxygen-containing atmosphere in the presence of a catalyst system which comprises a catalytically effective amount of iron oxide on alumina at a temperature in the range of between about 300° C. and 375° C. at atmospheric pressure.

27. A process in accordance with claim 26 wherein said catalyst system includes a catalytically effective amount of silver oxide disposed on said alumina.

* * * * *